United States Patent [19]

Johnston et al.

[11] Patent Number: 5,194,281
[45] Date of Patent: Mar. 16, 1993

[54] POLYOL FATTY ACID POLYESTERS WITH REDUCED TRANS DOUBLE BOND LEVELS AND PROCESS FOR MAKING

[75] Inventors: Robert W. Johnston, Sharonville; Josephine L. Kong-Chan, Cincinnati; Richard G. Schafermeyer, Cincinnati; Paul Seiden, Cincinnati, all of Ohio

[73] Assignee: The Procter & Gamble Company, Cincinnati, Ohio

[21] Appl. No.: 887,426

[22] Filed: May 21, 1992

Related U.S. Application Data

[63] Continuation of Ser. No. 590,023, Oct. 2, 1990, abandoned, which is a continuation-in-part of Ser. No. 421,867, Oct. 16, 1989, abandoned.

[51] Int. Cl.$^5$ .................. A23D 7/00; C07H 13/02
[52] U.S. Cl. ........................... 426/531; 426/549; 426/565; 426/601; 426/603; 426/611; 426/637; 426/804; 536/119; 536/124
[58] Field of Search ............... 426/531, 549, 565, 601, 426/603, 611, 637, 804; 536/119, 124

[56] References Cited

U.S. PATENT DOCUMENTS

| | | |
|---|---|---|
| 3,600,186 | 8/1971 | Mattson et al. |
| 3,963,699 | 6/1976 | Rizzi et al. |
| 4,005,195 | 1/1977 | Jandacek . |
| 4,005,196 | 1/1977 | Jandacek et al. |
| 4,517,360 | 5/1985 | Volpenhein . |

FOREIGN PATENT DOCUMENTS

| | | |
|---|---|---|
| 0132293 | 1/1985 | European Pat. Off. |
| 0233856 | 2/1987 | European Pat. Off. |
| 0235836 | 2/1987 | European Pat. Off. |
| 0236288 | 2/1987 | European Pat. Off. |
| 0272759 | 6/1988 | European Pat. Off. |
| 0350981 | 1/1990 | European Pat. Off. |

OTHER PUBLICATIONS

The Olestra Food Additive Petition (Procter & Gamble), published May 7, 1987.
Rizzi et al., "A Solvent-free Synthesis of Sucrose Polyesters", J. Amer. Oil Chem. Soc., 55(4), pp. 398-401 (Apr. 1978).
Mattson et al., "The Effect of a Non-Absorbable Fat, Sucrose Polyester, on the Metabolism of Vitamin A by the Rat", J. Nutrition, 109(10), pp. 1688-1693 (Oct. 1979).

Primary Examiner—Joseph Golian
Assistant Examiner—Evan Federman
Attorney, Agent, or Firm—Tara M. Rosnell; Eric W. Guttag; John M. Howell

[57] ABSTRACT

This invention relates to polyol fatty acid polyester compositions having improved physiological properties, organoleptic properties (i.e. mouth feel), liquid/solid stability and chemical stability. These polyol fatty acid polyesters are characterized in that (a) not more than about 0.6% of the fatty acid groups contain three or more double bonds, not more than about 20% of the fatty acid groups contain two or more double bonds, and not more than about 35% of the fatty acid double bonds are trans double bonds; (b) the polyesters have an iodine value between about 15 and about 60; and (c) the solid fat content/liquid solid stability ratio is not greater than 0.25. This invention also relates to a process for preparing these improved polyol polyester compositions.

51 Claims, No Drawings

POLYOL FATTY ACID POLYESTERS WITH REDUCED TRANS DOUBLE BOND LEVELS AND PROCESS FOR MAKING

CROSS REFERENCE TO RELATED APPLICATIONS

This is a continuation of application Ser. No. 07/590,023, filed on Oct.2, 1990 now abandoned, which is a continuation-in-part of application Ser. No. 421,867 filed on Oct. 16, 1989 now abandoned.

TECHNICAL FIELD

This invention relates to polyol fatty acid polyester compositions useful as low calorie fat substitutes. The invention particularly relates to polyol fatty acid polyester compositions having improved physiological properties, organoleptic properties (i.e. mouth feel), liquid/solid stability, and chemical stability. This invention also relates to a process for preparing improved polyol polyester compositions.

BACKGROUND OF THE INVENTION

The consumption of excessive amounts of edible vegetable oils and animal fats (i.e. triglycerides) has been linked to health problems such as obesity and heart disease. Therefore, there is increasing interest in fat substitutes that can be used as replacements for triglyceride fats in the diet.

Polyol fatty acid polyesters are known for use as fat substitutes in foods. U.S. Pat. No. 3,600,186 to Mattson et al. discloses low calorie, fat-containing, food compositions in which at least a portion of the triglyceride content is replaced with a sugar or sugar alcohol fatty acid ester, the polyester having at least four fatty acid ester groups with each fatty acid having from 8 to 22 carbon atoms. The polyesters are said to be useful in food products such as salad oil, cooking oil, plastic shortening, fried foods, cakes, breads, mayonnaise, margarine, and dairy products.

U.S. Pat. No. 4,005,196 to Jandacek et al. discloses the low calorie fat-containing food compositions of the type disclosed in the Mattson et al. patent, in combination with fat-soluble vitamins selected from the group consisting of vitamin A, vitamin D, vitamin E and vitamin K.

It is known that regular ingestion of moderate to high levels of liquid polyol polyesters can produce an undesirable "oil loss" effect, namely, leakage of the polyesters through the anal sphincter. U.S. Pat. No. 4,005,195 to Jandacek describes a means of preventing the undesirable oil loss effect through the addition to the polyesters of anti-anal leakage agents. The anti-anal leakage agents include solid fatty acids (melting point 37° C. or higher) and their triglyceride source, and solid polyol fatty acid polyesters.

The use of solid triglycerides or solid polyesters as anti-anal leakage agents for liquid polyesters has drawbacks when the polyesters are used in food compositions. A polyester or triglyceride having a solids content high enough to prevent anal leakage, typically tastes waxy in the mouth when ingested. It would be desirable to have a fat substitute that is still an effective substitute for triglyceride fats to make low calorie foods, but that also has a very low solids content so that it does not taste waxy in the mouth. At the same time, it is critical that this fat substitute not produce an undesirable oil-loss side effect.

European Patent Application 0,236,288 to Bernhardt, published Sep. 9, 1987, discloses polyol fatty acid polyesters that are highly resistant to anal leakage even at relatively low levels of solids. This benefit is achieved by polyesters that have a relatively high rheological profile at body temperature. Unfortunately, even the polyol polyesters disclosed by this European Application are not ideal for producing a non-waxy taste impression in foods. Furthermore, the specific polyol polyesters given as examples have poor oxidative stability. The polyesters of the Bernhardt application preferably have a solid fat content at body temperature of at least about 5%, and their viscosity at body temperature is at least about 25 poise at a shear rate of 10 seconds$^{-1}$. It would be desirable to have polyol fatty acid polyesters with improved taste impression in combination with oxidative stability.

Oils, such as soybean oil, are often hardened to reduce the degree of polyunsaturation. These hardened oils exhibit improved oxidative stability. One characteristic of typical hardened oils, is a high amount of trans-double bonds in the fatty acid chains. European Patent Application 0,235,836 to Bodor et al., published Sep. 9, 1987, discloses polyol fatty acid polyesters with improved oxidative stability. This benefit is achieved by polyesters that have a relatively high level of trans-unsaturated fatty acid chains.

As the level of trans-double bonds increases, the crystal size of the corresponding partially hardened composition also increases. It has been observed that large crystals correspond to a product with poor liquid-solid stability, i.e. mixtures of the solid and liquid polyesters do not remain homogeneous. This can result in poor anti-anal leakage control. Accordingly, it would be highly desirable to have a polyol polyester composition with a high degree of oxidative stability in combination with a high degree of liquid-solid stability resulting from small crystals.

Therefore, it is an object of the present invention to provide a polyol polyester composition with a low rheological profile which exhibits little or no "oil loss" effect.

It is also an object of the present invention to provide a polyol polyester composition with a high degree of oxidative stability. Accordingly, this composition exhibits a more stable flavor, a more stable color, and a minimal potential for undesirable reactions in the manufacturing process.

It is also an object of the present invention to provide a polyol polyester with a low ratio of solid fat content to liquid/Solid stability.

It is also an object of the present invention to produce a polyol polyester composition with low levels of solids at body temperature to minimize waxiness.

These and other objects of the present invention will become evident from the disclosures herein.

SUMMARY OF THE INVENTION

Polyol fatty acid polyesters are disclosed that are resistant to anal leakage even at very low solids levels and at relatively low viscosity at body temperature. These polyesters also exhibit good oxidative stability. The polyesters are particularly useful as nonwaxy-tasting fat substitutes in low calorie foods. Specifically, the invention is a composition of matter comprising a polyol fatty acid polyester fat substitute, the polyols having at least 4 hydroxyl groups and the polyol polyesters having at least 4 fatty acid groups, each fatty acid group having from about 2 to about 24 carbon atoms, wherein: (a) not more than about 0.6% of the fatty acids contain three or more double bonds, not more than about 20% of the fatty acids contain two or more double bonds, and not more than about 35% of the fatty acid double bonds are trans double bonds; (b) the polyesters have an iodine value between about 15 and about 60; and (c) the ratio of solid fat content to liquid/solid stability is not greater than 0.25.

The present invention also relates to a process for preparing improved polyolpolyester compositions wherein the polyesters are made by esterifying a polyol with a mixture of fatty acids from a primary source oil and a secondary fully hydrogenated source oil in a ratio between about 20:80 and about 80:20, the primary source oil having an iodine value between about 65 and about 100, and the fully hydrogenated oil having an iodine value between about 1 and about 12. These polyol polyesters can also be prepared by esterifying a polyol with a primary source oil stream; esterifying a polyol with another source oil stream; and blending the resulting polyol polyesters.

DEFINITIONS

All parts, percentages and ratios used herein are by weight unless otherwise indicated.

The term "sugar" is used herein in its conventional sense as generic to mono- and disaccharides. Trisaccharides and polysaccharides are also contemplated by the present invention, but are not preferred. The term "sugar alcohol" is also used in its conventional sense as generic to the reduction product of sugars wherein the aldehyde or ketone group has been reduced to an alcohol. The fatty acid ester compounds are prepared by reacting a monosaccharide, disaccharide or sugar alcohol with fatty acids as discussed below.

As used herein, the term "polyol" relates to moieties such as sugars as well as sugar alcohols, and other sugar derivatives (e.g. alkyl polyglycosides), that contain hydroxyl groups.

As used herein, the term "polyol fatty acid polyester" or "polyol polyester" relates to compositions comprised of polyols and fatty acids.

Examples of suitable monosaccharides are those containing 4 hydroxyl groups such as xylose, arabinose, and ribose; the sugar alcohol derived from xylose, i.e., xylitol, is also suitable. The monosaccharide erythrose is not suitable for the practice of this invention since it only contains 3 hydroxyl groups; however, the sugar alcohol derived from erythrose, i.e. erythritol, contains 4 hydroxyl groups and is thus suitable. Among 5 hydroxyl-containing monosaccharides that are suitable for use herein are glucose, mannose, galactose, and fructose. A sugar alcohol derived from glucose, i.e., sorbitol, contains 6 hydroxyl groups and is also suitable as the alcohol moiety of the fatty acid ester compound. Examples of suitable disaccharides are maltose, lactose, and sucrose, all of which contain 8 hydroxyl groups. Examples of trisaccharides include raffinose and maltotriose. Examples of other suitable polyols include pentaerythritol, diglycerol, triglycerol, alkyl glycosides and polyvinyl alcohols. The preferred polyol is sucrose.

As used herein, "$C_{x:y}$" relates to fatty acid groups where x is the carbon chain length and y is the number of double bonds.

DETAILED DESCRIPTION OF THE INVENTION

Contrary to prior teachings, it has been discovered that specific polyester compositions which are low in trans-double bonds can provide oxidative stability in combination with liquid/solid stability. Additionally, these compositions are useful as dietary fat substitutes and exhibit little or no "oil loss" effect and a non-waxy taste impression.

It has been observed that polyol fatty acid polyesters according to the present invention rapidly form small crystals during the solidification process. For a given level of solids, smaller crystals provide a relatively larger surface area, and they have been found to provide better liquid-entrainment properties (e.g., cohesiveness and viscosity) than larger crystals. As a result, the polyester has better anal leakage control properties. This development allows the achievement of anal leakage control with low levels of solids, which in turn minimizes the waxy impression of solid fat when eaten.

The low level of polyunsaturation in the present polyol polyesters provide improved chemical stability relative to polyol polyesters made from most unhydrogenated or nonspecific partially hydrogenated fatty acid sources. This provides highly desirable and stable flavor and color properties to the polyol polyesters. It also minimizes the potential for undesirable side reactions to occur in the manufacturing process, which can adversely affect the progress of the reaction for preparing polyesters and quality of the finished polyesters.

Specifically, the present invention is a composition of matter comprising a polyol fatty acid polyester fat substitute, preferably selected from the group consisting of sugar fatty acid polyesters, sugar alcohol fatty acid polyesters, and mixtures thereof, the polyol (e.g. sugars and sugar alcohols) containing at least 4 hydroxyl groups (preferably from about 4 to about 8 hydroxyl groups), and the polyol polyester containing least 4 fatty acid groups (preferably from about 4 to about 8 fatty acid groups), with each fatty acid group having from about 2 to about 24 carbon atoms, wherein:

(a) not more than about 0.6% of the fatty acids contain three or more double bonds, not more than about 20% of the fatty acids contain two or more double bonds, and not more than about 35% of the fatty acid double bonds are trans double bonds;

(b) the polyesters have an iodine value between about 15 and about 60; and (c) the ratio of solid fat content to liquid/solid stability is less than 0.25.

In preparing the polyol (e.g. sugar or sugar alcohol) fatty acid polyesters of the present invention a polyol (e.g. sugar or sugar alcohol) compound, such as those identified above, must be esterified with a mixture of fatty acids having from about 2 to about 24 carbon atoms. Preferably, the mixture of fatty acids have from about 8 to about 24 carbon atoms. Examples of such fatty acids are caprylic, capric, lauric, myristic, myristoleic, palmitic, palmitoleic, stearic, oleic, elaidic, ricinoleic, linoleic, linolenic, eleostearic, arachidic, behenic, and erucic. The fatty acids can be derived from suitable naturally occurring or synthetic fatty acids and can be saturated or unsaturated, including positional and geometric isomers.

Fatty acids per se or naturally occurring fats and oils can serve as the source for the fatty acid component in the polyol (e.g. sugar or sugar alcohol) fatty acid ester.

For example, rapeseed oil provides a good source for $C_{22}$ fatty acid. $C_{16}$–$C_{18}$ fatty acid can be provided by tallow, soybean oil, or cottonseed oil. Shorter chain fatty acids can be provided by coconut, palm kernel, or babassu oils. Corn oil, lard, olive oil, palm oil, peanut oil, safflower seed oil, high oleic safflower seed oil, sesame seed oil, canola oil, sunflower seed oil, and high oleic sunflower seed oil, are examples of other natural oils which can serve as the source of the fatty acid component.

A characterizing feature of the polyol (e.g. sugar or sugar alcohol) fatty acid polyesters useful in this invention is that they predominantly contain at least 4 fatty acid ester groups, typically from about 4 to about 8 fatty acid ester groups. Sugar or sugar alcohol fatty acid polyester compounds that contain 3 or less fatty acid ester groups are digested in the intestinal tract much in the manner as ordinary triglyceride fats, but sugar or sugar alcohol fatty acid polyester compounds that contain four or more fatty acid ester groups are digested to a lesser extent and thus have the desired low calorie properties for use in this invention.

Highly preferred low calorie fat materials according to this invention are sucrose fatty acid polyesters. Preferred sucrose fatty acid polyesters have the majority of their hydroxyl groups esterified with fatty acids. Preferably at least about 85%, and most preferably at least about 95%, of the sucrose fatty acid polyesters are selected from the group consisting of octaesters, heptaesters and hexaesters, and mixtures thereof. Preferably, no more than about 40% of the esters are hexaesters or heptaesters, and at least about 60% of the sucrose fatty acid polyesters are octaesters. More preferably, no more than about 30% of the esters are hexaesters or heptaesters. Most preferably, at least about 70% of the polyesters are octaesters. It is also most preferred that the polyesters have a total content of penta-and lower esters of not more than about 3%.

Not more than about 0.6%, preferably not more than about 0.3% of the fatty acids of the polyol polyester contain three or more double bonds and not more than about 20% of the fatty acids contain two or more double bonds. Furthermore, preferably from 0 to about 20% of the fatty acids are $C_{16:0}$.

Additionally, not more than about 35% of the fatty acid double bonds are trans configurated double bonds. The percent trans fatty acid double bonds is calculated as follows:

$$P = \frac{D_{trans}}{D_{total}} \times 100\%$$

where
P = percent trans fatty acid double bonds
$D_{trans}$ = number of trans double bonds
$D_{total}$ = total number of double bonds
Preferred fatty acid compositions according to the present invention comprise:
less than about 12% palmitic ($C_{16:0}$);
from about 30% to about 70% stearic ($C_{18:0}$);
from about 15% to about 60% oleic and elaidic ($C_{18:1}$);
less than about 12% linoleic ($C_{18:2}$); and
less than about 0.6% linolenic ($C_{18:3}$);
Most preferred fatty acid compositions according to the present invention comprises:
less than about 12% palmitic acid ($C_{16:0}$);
from about 40% to about 70% stearic acid ($C_{18:0}$);
from about 20% to about 50% oleic and elaidic acid ($C_{18:1}$);
less than about 12% linoleic acid ($C_{18:2}$);
less than about 0.6% linolenic acid ($C_{18:3}$);

Polyol polyesters suitable for use herein can be made by any one of a number of general syntheses. General methods for synthesizing polyol fatty acid polyesters include: transesterification of the sugar or sugar alcohol with methyl, ethyl, or glycerol fatty acid esters using a variety of catalysts; acylation of the sugar or sugar alcohol with a fatty acid chloride; acylation of the sugar or sugar alcohol with a fatty acid anhydride; and acylation of the sugar or sugar alcohol with a fatty acid, per se. As an example, the preparation of polyol fatty acid esters is described in U.S. Pat. Nos. 2,831,854; 3,600,186; 3,963,699; 4,517,360; and 4,518,772, all incorporated by reference herein.

A preferred method for preparing polyol polyesters according to the present invention involves using two source oil streams. A sugar or sugar alcohol is esterified with a mixture of fatty acids from a primary source oil and a fully hydrogenated secondary source oil in a ratio between about 20:80 and about 80:20, preferably between about 50:50 and about 75:25. The primary source oil has an iodine value between about 65 and about 100, preferably between about 75 and about 95, and the fully hydrogenated oil has an iodine value between about 1 and about 12, preferably between about 1 and about 10, and more preferably between 1 and about 8. The partially hydrogenated portion is derived by a special catalytic process which provides low levels of polyunsaturated fatty acids, and low levels of trans configurated double bonds. For example, the following hydrogenation conditions are suitable for use with sucrose polyesters: 0.02% by weight nickel catalyst, 40 psig pressure, 275° F. (135° C.) initial temperature, and 320° F. (160° C.) reaction temperature.

Another preferred method for preparing polyol polyesters according to the present involves:
(1) esterifying a polyol with a mixture of fatty acids from a primary source oil and a secondary fully hydrogenated source oil in a ratio between about 20:80 and about 80:20, the primary source oil having an iodine value between about 65 and about 100, and the fully hydrogenated oil having an iodine value between about 1 and about 12; and
(2) esterifying a polyol with a mixture of fatty acids from a tertiary source oil; and
(3) blending the esterified products of steps (1) and (2).

Preferably the iodine values of the primary source oil stream and secondary oil stream are about 75 to about 95 and about 1 to about 8 respectively. Preferably the iodine value for the tertiary source oil stream is about 65 to about 100, most preferably from about 75 to about 95.

The ratio of the fatty acid groups from the primary source oil stream to those from the secondary source oil stream is preferably between about 50:50 and 75:25.

Processes for preparing improved polyol polyesters prepared from three, four, or more source oil or esterified source oil streams are also contemplated by the present invention.

A more detailed example of a process for making preferred sucrose polyesters of the present invention is given in Example 1.

Source oils particularly suitable for use in the present invention include hardened and partially hardened canola, corn, safflower, high oleic safflower, soybean, peanut, sunflower or high oleic sunflower oils. Mixtures of these oils are also suitable.

The present polyol polyesters are resistant to anal leakage even though they have a low viscosity at body temperature. The polyesters have, at 100° F. (37.8° C.), a viscosity of at least about 2.5 poise after 10 minutes of steady shear at a shear rate of 10 seconds$^{-1}$, preferably a viscosity of at least about 5 poise, and most preferably at least about 15 poise. High viscosity products are not desirable, since they impart a wax-like taste. Product viscosities are typically less than 250 poise.

The present polyol polyesters have a high liquid/solid stability inasmuch as the liquid portion of the polyesters does not readily separate from the solid portion. Liquid/solid stability is quantified by Analytical Method II, described later. This property is critical for control of anal leakage. The polyesters have a liquid/solid stability of at least about 50%, preferably at least about 70%, and most preferably at least about 80%.

Moreover, the present polyol polyesters are very resistant to anal leakage even at very low levels of solids. The solid fat content (SFC) provides a reasonable approximation of the percent by weight solids of a particular fatty material at a given temperature. The present polyol polyesters have a ratio of solid fat content (measured at 98.6° F.) to liquid/solid stability of less than 0.25, preferably less than 0.20, most preferably less than 0.15.

Iodine value is a measure of the degree of unsaturation of fatty acids. The polyol fatty acid polyesters of this invention have an iodine value between about 15 and about 60, and preferably between about 20 and about 50.

The polyol fatty acid polyesters of the present invention can be used as a partial or total replacement for normal triglyceride fat in any fat-containing food composition to provide low calorie benefits. In order to obtain a significant low calorie effect, it is necessary that at least about 10% of the fat in the food composition, or 33% of the caloric value of the food, comprised of the polyol polyesters. Fat-containing food compositions wherein at least 30% of the fat is substituted with the present polyol polyesters are preferred; at least about 50% substitution is more preferred; and at least about 70% substitution is most preferred. On the other hand, very low calorie and thus highly desirable food compositions of the invention are obtained when the total fat comprises up to 100% of the polyesters of this invention, and from about 25% to 100% of the calories.

The polyol polyesters of the present invention can be used in conjunction with other polyol polyesters. In order to impart significant physiological, organoleptic and stability benefits to the resulting blend, these compositions should comprise at least about 30% of the present polyol polyesters, preferably at least about 50%, most preferably at least about 70%. The present polyol fatty acid polyesters, and particularly sucrose polyesters, are useful in a wide variety of food and beverage products. For example, the polyesters can be used in the production of baked goods in any form, such as mixes, shelf-stable baked goods, and frozen baked goods. Possible applications include, but are not limited to, cakes, brownies, muffins, bar cookies, wafers, biscuits, pastries, pies, pie crusts, and cookies, including sandwich cookies and chocolate chip cookies, particularly the storage-stable dual-textured cookies described in U.S. Pat. No. 4,455,333 of Hong & Brabbs. The baked goods can contain fruit, cream, or other fillings. Other baked good uses include breads and rolls, fried foods, sausages, meats, crackers, pretzels, pancakes, waffles, ice cream cones and cups, yeast-raised baked goods, pizzas and pizza crusts, french fries, baked farinaceous snack foods, and other baked salted snacks. Totally and partially fried food applications are also contemplated by the present invention.

In addition to their uses in baked goods, the polyol fatty acid polyesters can be used alone or in combination with other regular, reduced calorie or zero calorie fats to make shortening and oil products. The other fats can be synthetic or derived from animal or vegetable sources, or combinations of these. Shortening and oil products include, but are not limited to, shortenings, margarines, spreads, butter blends, lards, cooking and frying oils, salad oils, popcorn oils, salad dressings, mayonnaise, and other edible oils. They can be used in frying applications such as preparation of french fry potatoes, potato chips, corn chips, donuts, chicken, fish, and fried pies (e.g. turnovers). The polyol fatty acid polyesters of the present invention can also be used as a partial or total fat replacement in other fat-containing foods, e.g., ice cream, cheeses, etc.

The present polyol polyesters can also be fortified with vitamins and minerals, particularly the fat-soluble vitamins. U.S. Pat. No. 4,034,083 of Mattson (incorporated by reference herein) discloses polyol fatty acid polyesters fortified with fat-soluble vitamins. The fat-soluble vitamins include vitamin A, vitamin D, vitamin E, and vitamin K. Vitamin A is a fat-soluble alcohol of the formula $C_{20}H_{29}OH$. Natural vitamin A is usually found esterified with a fatty acid; metabolically active forms of vitamin A also include the corresponding aldehyde, acetate and acid, as well as provitamin Vitamin A's. Vitamin D is a fat-soluble vitamin well known for use in the treatment and prevention of rickets and other skeletal disorders. "Vitamin D" comprises sterols, and there are at least 11 sterols with vitamin D-type activity. Vitamin E (tocopherol) is a third fat-soluble vitamin which can be used in the present invention. Four different tocopherols have been identified (alpha, beta, gamma and delta), all of which are oily, yellow liquids, insoluble in water but soluble in fats and oils. Vitamin K exists in at least three forms, all belonging to the group of chemical compounds known as quinones. The naturally occurring fat-soluble vitamins are $K_1$ (phylloquinone), $K_2$ (menaquinone), and $K_3$ (menadione). The amount of the fat-soluble vitamins employed herein to fortify the present polyol fatty acid polyesters can vary. If desired, the polyesters can be fortified with a recommended daily allowance (RDA), or increment or multiple of an RDA, of any of the fat-soluble vitamins or combinations thereof. It is preferred that shortenings and oils containing up to 35% by weight of the present sucrose fatty acid polyesters be supplemented with 1.1 mg. vitamin E in the form of d-alpha-tocopherol acetate per gram of sucrose polyester. If used for deep frying, the shortenings and oils preferably contain 0.88 mg. vitamin E per gram of sucrose polyester.

Vitamins that are nonsoluble in fat can similarly be included in the present polyol fatty acid polyesters. Among these vitamins are the vitamin B complex vitamins, vitamin C, vitamin G, vitamin H, and vitamin P. The minerals include the wide variety of minerals known to be useful in the diet, such as calcium, magnesium, and zinc. Any combination of vitamins and minerals can be used in the present polyol polyesters.

The present polyol fatty acid polyesters are particularly useful in combination with particular classes of food and beverage ingredients. For example, an extra calorie reduction benefit is achieved when the polyesters are used with noncaloric or reduced calorie sweeteners alone or in combination with bulking agents. Noncaloric or reduced calorie sweeteners include, but are not limited to, aspartame; saccharin; alitame, thaumatin; dihydrochalcones; cyclamates; steviosides; glycyrrhizins, synthetic alkoxy aromatics, such as Dulcin and P-4000; sucrolose; suosan; miraculin; monellin; sorbitol, xylitol; talin; cyclohexylsulfamates; substituted imidazolines; synthetic sulfamic acids such as acesulfame, acesulfam-K and n-substituted sulfamic acids; oximes such as perilartine; rebaudioside-A; peptides such as aspartyl malonates and succanilic acids; dipeptides; amino acid based sweeteners such as gem-diaminoalkanes, meta-aminobenzoic acid, L-aminodicarboxylic acid alkanes, and amides of certain alpha-aminodicarboxylic acids and gem-diamines; and 3-hydroxy-4-alkyloxyphenyl aliphatic carboxylates or heterocyclic aromatic carboxylates.

The polyol fatty acid polyesters can be used in combination with other noncaloric or reduced calorie fats, such as branched chain fatty acid triglycerides, triglycerol ethers, polycarboxylic acid esters, sucrose polyethers, neopentyl alcohol esters, silicone oils/siloxanes, and dicarboxylic acid esters. Other partial fat replacements useful in combination with the fat materials are triglycerides containing medium and long chain saturated fatty acids as disclosed in European patent application 0322027 to Seiden, published Jun. 28, 1989 (incorporated herein by reference), medium chain triglycerides, highly esterified polyglycerol esters, acetin fats, plant sterol esters, polyoxyethylene esters, jojoba esters, mono/diglycerides of fatty acids, and mono/diglycerides of short-chain dibasic acids.

Bulking or bodying agents are useful in combination with the polyol polyesters in many food compositions. The bulking agents can be nondigestible carbohydrates, for example, polydextrose and cellulose or cellulose derivatives, such as carboxymethylcellulose, carboxyethylcellulose, hydroxypropylcellulose, methylcellulose and microcrystalline cellulose. Other suitable bulking agents include gums (hydrocolloids), starches, dextrins, fermented whey, tofu, maltodextrins, polyols, including sugar alcohols, e.g. sorbitol and mannitol, and carbohydrates, e.g. lactose.

Similarly, food and beverage compositions can be made that combine the present polyol fatty acid polyesters with dietary fibers to achieve the combined benefits of each. By "dietary fiber" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for example, by bacterial synthesis). Commercial fibers such as purified plant cellulose, or cellulose flour, can also be used. Naturally occurring fibers include fiber from whole citrus peel, citrus albedo, sugar beets, citrus pulp and vesicle solids, apples, apricots, and watermelon rinds.

These dietary fibers may be in a crude or purified form. The dietary fiber used may be of a single type (e.g. cellulose), a composite dietary fiber (e.g. citrus albedo fiber containing cellulose and pectin), or some combination of fibers (e.g. cellulose and a gum). The fibers can be processed by methods known to the art.

Of course, judgment should be exercised to make use of appropriate polyol fatty acid polyesters and combinations of the polyesters with other food ingredients. For example, a combination of sweetener and polyol polyester would not be used where the specific benefits of the two are not desired. The polyesters and polyester/ingredient combinations are used where appropriate, and in the proper amounts.

Many benefits are obtained from the use of the present polyol fatty acid polyesters in food and beverage compositions, either when used alone or in combination with the ingredients discussed above. A very important health benefit of the present polyesters derives from the fact that they are low in dietary saturated fatty acids. Another primary benefit is the calorie reduction achieved when the polyesters are used as a total or partial fat replacement. This calorie reduction can be increased by using combinations of the present polyol polyesters with reduced calorie sweeteners, bulking agents, or other reduced calorie or noncaloric fats. Another benefit which follows from this use is a decrease in the total amount of fats in the diet. Foods or beverages made with the polyol polyesters instead of triglyceride fats will also contain less cholesterol, and the ingestion of these foods can lead to reduced serum cholesterol and thus reduced risk of heart disease.

A related benefit is that the use of the polyol fatty acid polyesters allows the production of foods and beverages that are stable in terms of shelf stability and penetration stability. Compositions made with the polyesters have acceptable organoleptic properties, particularly taste and texture.

Dietary foods can be made with the polyol fatty acid polyesters, to meet special dietary needs, for example, of persons who are obese, diabetic, or hypercholesterolemic or are on a fat-restricted diet. The polyesters can be a major part of a low-fat, low-calorie, low-cholesterol diet, and they can be used alone or in combination with drug therapy or other therapy. Combinations of food or beverage products made with the polyol fatty acid polyesters can be used as part of a total dietary management regimen, based on one or more of these products, containing the polyesters alone or in combination with one or more of the above-mentioned ingredients, to provide one or more of the above-mentioned benefits.

This discussion of the low calorie fat material uses, combinations, and benefits, is not intended to be limiting or all-inclusive. It is contemplated that other similar uses and benefits can be found that will fall within the spirit and scope of this invention.

ANALYTICAL METHODS

I. Viscosity Measurement of the Polyol Fatty Acid Polyesters

A. Sample Preparation

The polyester sample is melted in a hot water bath at greater than 190° F. (87.8° C.). The melted polyester is thoroughly mixed and ten grams of the melted sample is weighed into a vial. The vial is covered and then heated in a hot water bath to greater than 190° F. (87.8° C.). The sample is then allowed to recrystallize at 100° F. ±0.5° F. (37.8° C. ±0.3° C.) for 24 hours in a constant temperature room. After the 24 hour time period has elapsed, the sample is taken to the viscometer and the viscosity is measured.

B. Ferranti-Shirley Viscometer Operation Procedure

A Ferranti-Shirley viscometer (Ferranti Electric, Inc., 87 Modular Ave., Commack, NY 11725) equipped with a 600 g torque spring is used for the viscosity measurement. A cone is put into place, and the viscometer temperature is adjusted to 100° F. (37.8° C.). The chart recorder is calibrated, and the gap between the cone and plate is set. The cone speed is checked, and the cone and plate temperatures are equilibrated to 100° F. (37.8° C.). The panel controls are set. Sufficient sample is placed between the plate and the cone so that the gap is completely filled. The temperature is allowed to stabilize at 100° F. (37.8° C.) for about 30 seconds. The test is started by selecting the rpm for 10 seconds$^{-1}$ shear rate and recording on the strip chart recorder. The shear stress is recorded at 10 minutes after the point at which the shear stress reaches the maximum value. Viscosity (poise) = shear stress (dynes/cm$^2$) divided by shear rate (seconds$^{-1}$).

II. Liquid/Solid Stability Measurement of the Polyol Fatty Acid Polyesters

The sample of the test composition is heated in a hot water bath at greater than 190° F. (87.8° C.) until it completely melts and is then thoroughly mixed. The sample is then poured to capacity into 4.4 ml centrifuge tubes at 100° F. (37.8° C.) ±0.5° F. The samples then are allowed to recrystallize for 24 hours at 100° F. (37.8° C.) in a constant temperature room. The samples are then centrifuged at 60,000 rpm in a Beckman Model L870M centrifuge having a Beckman Model SW60 head (Beckman Instruments, Palo Alto, California) for one hour at 100° F. (37.8° C.). The maximum force on the samples is 485,000 G's (i.e. the force at the bottom of the centrifuge tube). The percent of the liquid oil is measured by comparing the relative heights of the liquid and solid phases. The liquid/solid stability is calculated using the following equation: Liquid/solid stability = total sample height (mm) − liquid oil height (mm) × 100/total sample height (mm)

III. Solid Fat Content Measurement

Before determining SFC values, the polyol fatty acid polyester sample is heated to a temperature of 140° F. (60° C.) or higher for at least 0.5 hours or until the sample is completely melted. The melted sample is then tempered as follows: at 80° F. (26.7° C.) for 15 minutes; at 32° F. (0° C.) for 15 minutes; at 80° F. (26.7° C.) for 30 minutes; and at 32° F. (0° C.) for 15 minutes. After tempering, the SFC value of the sample at temperatures of 50° F. (10° C.), 70° F. (21.1° C.), 80° F. (26.7° C.), 92° F. (33.3° C.), and 98.6° F. (37° C.) are determined by pulsed nuclear magnetic resonance (PNMR). The method for determining SFC values by PNMR is described in Madison and Hill, *J. Amer. Oil Chem. Soc.*. vol. 55 (1978), pp. 328-31 (herein incorporated by reference). Measurement of SFC by PNMR is also described in A.O.C.S. Official Method Cd. 16-81, *Official Methods and Recommended Practices of The American Oil Chemists Society.* 3rd Ed., 1987 (herein incorporated by reference).

IV. Fatty Acid Composition

Fatty acid composition (FAC) of the polyol fatty acid polyester sample is determined by gas chromatography, using a Hewlett-Packard Model 5880 gas chromatograph equipped with a flame ionization detector and a Hewlett-Packard Model 7673 automatic sampler. The chromatographic method used is described in *Official Methods and Recommended Practices of the American Oil Chemists Society.* 3rd Ed., 1987, Procedure Ce 1-62.

V. Ester Distribution of Polyesters

The relative distribution of the individual octa-, hepta-, hexa- and penta- esters, as well as collectively the tetra- through mono- esters, of the polyester samples can be determined using normal-phase high performance liquid chromatography (HPLC). A silica gel-packed column is used in this method to separate the polyester sample into the respective ester groupings noted above. Hexane and methyl-t-butyl ether are used as the mobile phase solvents. The ester groupings are quantitated using a mass detector (i.e., an evaporative light scattering detector). The detector response is measured and then normalized to 100%. The individual ester groups are expressed as a relative percentage.

IV. Measurement of Polyunsaturated Fatty Acids

The percentage of polyunsaturated fatty acids is simply calculated arithmetically from the fatty acid composition, where polyunsaturated fatty acids are defined as having two or more double bonds.

V. Measurement of Trans Configurated Fatty Acids

The trans content, as a percentage of the double bonds of the unsaturated fatty acids in the polyester sample, is determined by infrared spectrophotometry (IR). The IR method used is described in Madison et al, "Accurate Determination of trans Isomers in Shortenings and Edible Oils by Infrared Spectrophotometry." *J. Am. Oil Chem,.* Vol. 59, No. 4 (1982), pp. 178-181. The trans value obtained by IR, together with the FAC of the polyester sample, can be used to calculate the ratio of cis:trans double bonds.

The following example is intended to be further illustrative but not limiting of the present invention.

EXAMPLE 1

Refined soybean oil is hardened to an iodine value between 1 and 8. The oil is hardened by hydrogenation using 0.01% to 0.2% by weight nickel catalyst, under 0-40 psig pressure, at a temperature of 300° F. (149° C.) to 400° F. (204° C.). The hardened oil is then bleached, and put into a storage tank. The hardened soybean oil has the following characteristics: Fatty acid composition: 10-14% $C_{16:0}$, 83-88% $C_{18:0}$, 0.2-2% $C_{18:1}$, 0.2-0.4% $C_{18:2}$ and 0% $C_{18:3}$. Iodine value: 1-8. Free fatty acid content: 0.1-1.0%. Lovibond Y color: 8.0. Lovibond R color: 0.9.

A second batch of refined soybean oil is partially hardened to an iodine value between 80 and 85. Hydrogenation conditions are as follows: 0.02% by weight nickel catalyst, 40 psig pressure, 275° F. (135° C.) initial temperature, and 320° F. (160° C.) reaction temperature. The partially hardened oil is then bleached, and put into a storage tank. This oil has the following characteristics: Fatty acid compositions: 9.9% $C_{16:0}$, 6.1% $C_{18:0}$, 67.6% $C_{18:1}$, 14.8% $C_{18:2}$, and 0.9% $C_{18:3}$. Solid fat content: 18.1% at 50° F., 7.1% at 70° F., 3.08% at 80° F., 0% at 92° F., and 0% at 105° F. Percent trans configurated double bonds: 27-30%. Iodine value: 80-85. Free fatty acid content: 0.19%. Lovibond Y color: 16. Lovibond R color: 0.9.

The partially hardened oil and the hardened oil are blended together in a 70:30 ratio of partially hardened to hardened oil. The blended oil is deodorized at a temperature of 375° F.–475° F. (190° C.–246° C.). Then the blended oil is converted into methyl esters through an esterification process in which the oil is mixed with methanol, a sodium methoxide catalyst is added, and the reaction is continued until all the triglycerides are converted to methyl esters. The catalyst is neutralized with phosphoric acid, and the product is centrifuged to separate the esters from the product glycerol. The esters are distilled to remove unsaponifiable materials. These are esters "A".

About 95.3 kg of methyl esters of a refined soybean oil, fully hardened to an IV of about 2, are mixed with 295 kg of methanol and 20 kg of potassium hydroxide in a stainless steel batch reactor. This mixture is heated to about 145° F. (63° C.) with agitation for 1 to 3 hours at atmospheric pressure. During this time, a portion of the methyl esters are saponified to form soap.

About 553 kg of methyl esters of a refined soybean oil, fully hardened to an IV of about 2, are mixed with about 987 kg of the esters "A" to make ester blend "B". About 592 kg. of ester "B" are added to the previously made soap mixture.

About 136 kg. of granular sucrose are then added to give a 5:1 molar ratio of methyl ester to sucrose. Potassium carbonate is then added to the mixture (approx. 0.5 wt. percent of the reaction mix) to catalyze the transesterification. This mixture is agitated and slowly heated at atmospheric pressure until the temperature reaches about 275° F. (135° C.). This is to remove the methanol. A vacuum is then pulled and the mixture agitated for up to 4 hours to form the mono-, di- and trisucrose esters. Small quantities of tetra- and pentaesters are also formed during this stage. Additional methyl ester "B" (944 kg) which has been preheated to 275° F. (135° C.) is added to bring and maintain the molar ratio of the esters to sucrose to 14–15:1. Additional potassium carbonate is then added twice to the mixture (approx. 0.5 wt. percent of the initial reaction mix). When the reaction conditions stabilize at 275° F. (135° C.), a nitrogen sparge is used to improve agitation and promote methanol stripping. This second reaction stage lasts approximately 4 to 13 hours.

The reaction mixture is then cooled under nitrogen to between 149° F. (65° C.) and 185° F. (85° C.). The crude reaction mixture is agitated with about 95 kg water. The hydrated crude reaction mixture is passed through a centrifuge to separate a heavy and a light phase. The heavy phase which contains the soaps, excess sugars and potassium carbonate is discarded. The light phase was then washed with an additional 290 kg of water.

The light phase which contains methyl esters and the sucrose polyester is then dried to remove moisture at 176° F. (80° C.) under 70 mm Hg or less vacuum for 30 to 60 minutes. Filtrol 105 (1.0 wt. percent) is added and the mix is agitated at 167° F. (75° C.) to 185° F. (85° C.). The slurry is separated by filtration or other means until there is less than 0.1 wt. percent fines. The liquid is then passed through a 1 micromillimeter filter.

The refined and bleached reaction mix is then passed through a stainless steel wiped-film evaporator or other suitable equipment to distill off the bulk of the methyl esters. The distillation takes place at 392° F. (200° C.) to 455° F. (235° C.) under approximately 3 mm Hg of vacuum.

The sucrose polyester is then deodorized by passing downward through a stainless steel packed column deodorizer or other suitable device at 392° F. (200° C.) to 482° F. (250° C.) under a vacuum of about 5 mm Hg or less. Steam is introduced to the bottom of the column and passes counter-currently to the sucrose polyester. Feed rates and temperature are adjusted until the methyl ester content of the sucrose polyester is below 1000 ppm. The mixture is then cooled to between 149° F. (65° C.) to 185° F. (85° C.) and passed through a 1 micromillimeter filter. The sucrose polyester is stored in clean stainless steel drums.

Sucrose polyester made according to this procedure has the following composition and properties:

| Fatty Acid Composition | |
| --- | --- |
| $C_{16}$ | 10.8% |
| $C_{17}$ | 0.2 |
| $C_{16:1}$ | 0.0 |
| $C_{18}$ | 47.7 |
| $C_{18:1}$ | 33.0 |
| $C_{18:2}$ | 7.2 |
| $C_{18:3}$ | 0.0 |
| $C_{20}$ | 0.3 |
| $C_{20:1}$ | 0.1 |
| $C_{22}$ | 0.1 |
| $C_{24}$ | 0.2 |
| Iodine Value | 41.2 |
| Ester Distribution | |
| Octa | 92.8% |
| Hepta | 7.2 |
| Hexa | <0.1 |
| Penta | <0.1 |
| Lower | <0.1 |
| Solid Fat Content | |
| 98.6° F. (37° C.) | 10.4% |
| Viscosity After 10 min. steady shear at shear rate of 10 seconds$^{-1}$ | 33.0 poise |
| Liquid/Solid Stability | 95% |
| Ratio of Solid Fat Content To Liquid/Solid Stability | 0.11 |
| Percent Polyunsaturated Fatty Acids | 7.2 |
| Percent Trans Double Bonds | 13.6 |

What is claimed is:

1. A composition of matter comprising a polyol fatty acid polyester fat substitute, wherein the polyol contains at least 4 hydroxyl groups and wherein the polyol polyester contains at least 4 fatty acid groups, each fatty acid group having from about 2 to about 24 carbon atoms, wherein:

(a) not more than about 0.6% of the fatty acids contain three or more double bonds, not more than about 20% of the fatty acids contain two or more double bonds, and not more than about 35% of the fatty acid double bonds are trans double bonds;

(b) the polyesters have an iodine value between about 15 and about 60; and (c) the ratio of solid fat content at 98.6° F. to liquid solid stability is less than 0.25.

2. A composition according to claim 1 wherein the polyol polyester is selected from the group consisting of sugar fatty acid polyesters, sugar alcohol polyesters, and mixtures thereof, said polyol polyester having from 4 to 8 fatty acid groups.

3. A composition according to claim 2 wherein the fatty acids further comprise from 0 to about 20% $C_{16:0}$.

4. A composition according to claim 3 wherein the fatty acids comprise:
   (1) less than about 12% $C_{16:0}$ fatty acid;
   (2) from about 30% to about 70% $C_{18:0}$ fatty acid;
   (3) from about 15% to about 60% $C_{18:1}$ fatty acid;
   (4) less than about 12% $C_{18:2}$ fatty acid; and
   (5) less then about 0.6% $C_{18:3}$ fatty acid; wherein not more than about 32% of the fatty acid double bonds are trans double bonds.

5. A composition according to claim 4 wherein the fatty acids comprise:
   (1) less than about 12% $C_{16:0}$ fatty acid;
   (2) from about 40% to about 70% $C_{18:0}$ fatty acid;
   (3) from about 20% to about 50% $C_{18:1}$ fatty acid;
   (4) less than about 12% $C_{18:2}$ fatty acid; and
   (5) from 0 to 0.6% $C_{18:3}$ fatty acid; wherein from about 13% to about 32% of the fatty acid double bonds are trans double bonds.

6. A composition according to claim 4 wherein the ratio of solid fat content at 98.6° F. to liquid/solid stability is not greater than 0.20.

7. A composition according to claim 6 wherein the ratio of solid fat content at 98.6° F. to liquid/solid stability is not greater than 0.15.

8. A composition according to claim 6 wherein the liquid/solid stability is at least about 50%.

9. A composition according to claim 7 wherein the liquid/solid stability is at least about 70%.

10. A composition according to claim 7 wherein the liquid/solid stability is at least 80%.

11. A composition according to claim 8 wherein the viscosity at 100° F. (37.8° C.) is at least 2.5 poise after 10 minutes of steady shear at a shear rate of 10 seconds$^{-1}$.

12. A composition according to claim 9 wherein the viscosity at 100° F. (37.8° C.) is at least about 5 poise.

13. A composition according to claim 10 wherein the viscosity at 100° F. (37.8° C.) is at least about 15 poise.

14. A composition according to claim 12 wherein not more than about 0.3% of the fatty acids contain 3 or more double bonds.

15. A composition according to claim 12 wherein the polyesters have an iodine value between about 20 and about 50.

16. A composition according to claim 4 wherein the polyol polyesters are made by esterifying a polyol with a mixture of fatty acids from a primary source oil and a secondary fully hydrogenated source oil in a ratio between about 20:80 and about 80:20, the primary source oil having an iodine value between about 65 and about 100, and the fully hydrogenated oil having an iodine value between about 1 and about 12.

17. A composition according to claim 16 wherein the primary source oil has an iodine value between about 75 and about 95, and the fully hydrogenated secondary oil has an iodine value between about 1 and about 8.

18. A composition according to claim 17 wherein the polyesters are made by esterifying a polyol with a mixture of fatty acids from a partially hydrogenated source oil and a fully hydrogenated source oil in a ratio between about 50:50 and about 75:25.

19. A composition according to claim 18 wherein the source oils are selected from the group comprising canola oil, corn oil, safflower oil, high oleic safflower, soybean oil, peanut oil, sunflower oil or high oleic sunflower oil.

20. A composition according to claim 19 wherein the polyol polyester is a sucrose fatty acid polyester.

21. A composition according to claim 20 wherein at least 85% of the sucrose fatty acid polyesters are selected from the group consisting of octaesters, heptaesters, hexaesters and mixtures thereof.

22. A composition according to claim 21 wherein at least 95% of the sucrose fatty acid polyesters are selected from the group consisting of octaesters, heptaesters, hexaesters and mixtures thereof.

23. A composition according to claim 22 having a total content of penta- and lower esters of not more than about 3%.

24. A composition according to claim 4 wherein the polyol polyesters are made by the steps comprising:
   (1) esterifying a polyol with a mixture of fatty acids from a primary source oil and a secondary fully hydrogenated source oil in a ratio between about 20:80 and about 80:20, the primary source oil having an iodine value between about 65 and about 100, and the fully hydrogenated oil having an iodine value between about 1 and about 12; and
   (2) esterifying a polyol with a mixture of fatty acids from a tertiary source oil; and
   (3) blending the esterified products of steps (1) and (2).

25. A composition according to claim 24 wherein the ratio of fatty acids from the primary source to the secondary source oil is between about 50:50 and 75:25.

26. A composition according to claim 25 wherein the source oils are selected from the group comprising canola oil, corn oil, safflower oil, high oleic safflower, soybean oil, peanut oil, sunflower oil, or high oleic sunflower oil.

27. A composition according to claim 26 wherein the polyol polyester is a sucrose fatty acid polyester.

28. A composition according to claim 27 wherein at least 85% of the sucrose fatty acid polyesters are selected from the group consisting of octaesters, heptaesters, hexaesters and mixtures thereof.

29. A composition according to claim 28 wherein at least 95% of the sucrose fatty acid polyesters are selected from the group consisting of octaesters, heptaesters, hexaesters and mixtures thereof.

30. A composition according to claim 29 having a total content of penta- and lower esters of not more than about 3%.

31. A composition according to claim 30 wherein the primary and tertiary source oils have iodine values between about 75 and 95 and the secondary oil has an iodine value between about 1 and 8.

32. A polyol polyester fat substitute comprising:
   (a) a polyol containing from 4 to 8 hydroxyl groups;
   (b) from 4 to 8 fatty acid groups;
   (c) from about 8 to about 22 carbon atoms in each fatty acid group;
   (d) not more than about 0.6% fatty acids containing three or more double bonds, not more than about 20% fatty acids containing two or more double bonds, and not more than about 35% of the double bonds being trans double bonds;
   (e) a liquid/solid stability of at least about 50;
   (f) an iodine value between about 15 and about 60;
   (g) a ratio of solid fat content at 98.6° F. to liquid/solid stability of less than 0.25;
   (h) a fatty acid composition comprising:
      (1) from about 4% to about 12% $C_{16:0}$ fatty acid;
      (2) from about 35% to about 68% $C_{18:0}$ fatty acid;
      (3) from about 15% to about 43% $C_{18:1}$ fatty acid;

(4) from about 2% to about 12% $C_{18:2}$ fatty acid; and
(5) from 0% to about 0.6% $C_{18:3}$ fatty acid;
(i) a viscosity at 100° F. (37.8° C.) of at least about 2.5 poise after 10 minutes of steady shear at a shear rate of 10 $sec^{-1}$.

33. A fat substitute according to claim 32 which is a sucrose fatty acid polyester.

34. A food composition comprising non-fat ingredients and fat ingredients, wherein at least about 30% of the total fat ingredients is a composition according to claim 33.

35. A food composition wherein at least about 50% of the total fat ingredients is a composition according to claim 33.

36. A food composition wherein at least about 75% of the total fat ingredients is a composition according to claim 33.

37. A food composition according to claim 34 wherein the food is a margarine.

38. A food composition according to claim 34 wherein the food is a shortening.

39. A food composition according to claim 34 wherein the food is a cooking oil.

40. A food composition according to claim 34 wherein the food is a mayonnaise.

41. A food composition according to claim 34 wherein the food is a salad dressing.

42. A food composition according to claim 34 wherein the food is a cookie.

43. A food composition according to claim 34 wherein the food is a cake.

44. A food composition according to claim 34 wherein the food is a frying fat.

45. A food composition according to claim 34 wherein the food is a salted snack.

46. A food composition according to claim 34 wherein the food is an ice cream.

47. A food composition according to claim 34 wherein the food is a french fry potato.

48. A composition according to claim 34 additionally comprising fat-soluble vitamins.

49. A process for producing a fat substitute selected from the group consisting of sugar fatty acid polyesters, sugar alcohol fatty acid polyesters, and mixtures thereof, the sugars and sugar alcohols containing from 4 to 8 hydroxyl groups and from 4 to 8 fatty acid groups, each fatty acid group having from about 2 to about 24 carbon atoms, the process comprising the steps of
(1) esterifying a polyol with a mixture of fatty acids from a primary source oil and a secondary fully hydrogenated source oil in a ratio between about 20:80 and about 80:20, the primary source oil having an iodine value between about 65 and about 100, and the fully hydrogenated oil having an iodine value between about 1 and about 12; and
(2) esterifying a polyol with a mixture of fatty acids from a tertiary source oil, the tertiary source oil having an iodine value of from about 65 to about 100; and
(3) blending the esterified products of steps (1) and (2). wherein the blended esterified product has:
(a) not more than about 0.6% fatty acids contain three or more double bonds, and not more than about 20% fatty acids containing two or more double bonds, not more than about 35% of the double bonds being trans double bonds;
(b) a liquid/solid stability of at least about 50%; and
(c) an iodine value between about 10 and about 60;
(d) a solid fat content at 98.6° F.:liquid solid stability ratio is less than 0.25;
(e) a fatty acid composition comprising:
(1) from about 4 to about 12% $C_{16:0}$ fatty acid;
(2) from about 35% to about 68% $C_{18:0}$ fatty acid;
(3) from about 15% to about 43% $C_{18:1}$ fatty acid;
(4) from about 2% to about 12% $C_{18:2}$ fatty acid;
(5) from 0% to about 0.6% $C_{18:3}$ fatty acid;and
(f) a viscosity at 100° F. (37.8° C.) of at least about 2.5 poise after 10 minutes of steady shear at a shear rate of 10 $sec.^{1}$.

50. A process according to claim 49 wherein the ratio of fatty acids from the primary source oil to the secondary source oil is between about 50:50 and about 75:25.

51. A process according to claim 50 wherein the primary and tertiary source oils have iodine values between about 75 and about 95, and the fully hydrogenated secondary oil has an iodine value between about 1 and about 8.

* * * * *